United States Patent
Ansari et al.

(10) Patent No.: US 11,578,034 B2
(45) Date of Patent: Feb. 14, 2023

(54) INTEGRATED PROCESS FOR PRODUCTION OF GLYCEROL CARBONATE (4-HYDROXYMETHYL-2-OXO-1, 3-DIOXOLANE) AND UREA

(71) Applicant: SABIC Global Technologies B.V., Bergen op Zoom (NL)

(72) Inventors: Mohammed Bismillah Ansari, Riyadh (SA); Vijay Dinkar Bodas, Riyadh (SA); Guillermo Leal, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/496,497

(22) PCT Filed: Mar. 7, 2018

(86) PCT No.: PCT/IB2018/051487
§ 371 (c)(1),
(2) Date: Sep. 23, 2019

(87) PCT Pub. No.: WO2018/189598
PCT Pub. Date: Oct. 18, 2018

(65) Prior Publication Data
US 2020/0024227 A1    Jan. 23, 2020

Related U.S. Application Data

(60) Provisional application No. 62/484,276, filed on Apr. 11, 2017.

(51) Int. Cl.
C07C 273/04 (2006.01)
C07C 269/00 (2006.01)
(Continued)

(52) U.S. Cl.
CPC ............ *C07C 273/04* (2013.01); *C01C 1/086* (2013.01); *C07C 269/00* (2013.01); *C07C 273/14* (2013.01); *C07D 317/36* (2013.01)

(58) Field of Classification Search
None
See application file for complete search history.

(56) References Cited

U.S. PATENT DOCUMENTS 4,436,668 A * 3/1984 Harder ................... C07C 68/00
                                                                    558/275
5,003,084 A * 3/1991 Su ......................... C07D 317/36
                                                                    549/229

(Continued)

FOREIGN PATENT DOCUMENTS

CN      102177148 A        9/2011
CN      102464646    *     5/2012     ........... C07C 317/36

(Continued)

OTHER PUBLICATIONS

Meessen ("Urea" Ullmann's Encyclopedia of Industrial Chemistry, published online Oct. 15, 2010, downloaded from https://onlinelibrary.wiley.com/doi/10.1002/14356007.a27_333.pub2 on Apr. 16, 2020, p. 657-695) (Year: 2010).*

(Continued)

*Primary Examiner* — Amy C Bonaparte
(74) *Attorney, Agent, or Firm* — Norton Rose Fulbright US LLP

(57) ABSTRACT

Systems and methods for integrated glycerol carbonate and/or urea production. This disclosure pertains to development of a process for production of glycerol carbonate and/or urea from ammonia, carbon dioxide and glycerol. The process integrates glycerol carbonate production into a urea production process. The urea produced in the production facility may be used to produce glycerol carbonate by reacting urea with glycerol. The ammonia generated by (Continued)

glycerol carbonate production may be recycled back to urea production. Unreacted urea from the glycerol carbonate production may be separated and recycled to the urea product stream. The systems and methods can reduce the cost for urea production and increase product value of the excessive glycerol produced from other chemical plants.

16 Claims, 2 Drawing Sheets

(51) Int. Cl.
  *C07C 273/14* (2006.01)
  *C07D 317/36* (2006.01)
  *C01C 1/08* (2006.01)

(56) References Cited

U.S. PATENT DOCUMENTS

| | | | | |
|---|---|---|---|---|
| 5,561,094 | A * | 10/1996 | Saleh | B01J 3/04 |
| | | | | 502/152 |
| 5,980,445 | A * | 11/1999 | Mizukami | C07C 68/00 |
| | | | | 558/274 |
| 6,025,504 | A | 2/2000 | Claude et al. | 549/229 |
| 6,392,078 | B1 * | 5/2002 | Ryu | C07C 68/00 |
| | | | | 558/277 |
| 6,495,703 | B1 | 12/2002 | Okutsu et al. | 549/229 |
| 8,314,259 | B2 | 11/2012 | Jung et al. | 549/229 |
| 8,921,261 | B2 * | 12/2014 | Lee | B01J 23/06 |
| | | | | 502/342 |
| 2006/0142607 | A1 * | 6/2006 | Ryu | C07C 68/00 |
| | | | | 558/277 |
| 2011/0245513 | A1 * | 10/2011 | Dubois | C07D 317/36 |
| | | | | 549/229 |

FOREIGN PATENT DOCUMENTS

| | | | | |
|---|---|---|---|---|
| CN | 104557553 | A | 4/2015 | |
| CN | 105664907 | * | 6/2016 | B01J 23/06 |
| CN | 106349207 | * | 1/2017 | C07D 317/36 |
| EP | 2174937 | A1 | 4/2010 | |
| KR | 20130121603 | * | 11/2013 | B01J 21/02 |
| KR | 20140014563 | A | 2/2014 | |
| KR | 2015131657 | A | 11/2015 | |
| WO | WO2010040786 | A2 | 4/2010 | |
| WO | WO2010097585 | * | 9/2010 | C07D 317/34 |
| WO | WO2014059961 | A1 | 4/2014 | |
| WO | WO2017035734 | A1 | 3/2017 | |

OTHER PUBLICATIONS

Climent ("Chemicals from biomass: Synthesis of glycerol carbonate by transesterification and carbonylation with urea and hydrotalcite catalysts. The role of acid-base pairs" J. of Catalysis, 269 (2010), p. 140-149) (Year: 2010).*
English language translation of KR1020130121603. (Year: 2013).*
Huntsman Corporation, JEFFSOL® Alkylene Carbonates, Technical Bulletin, 2001.
International Search Report and Written Opinion from PCT/IB2018/051487 dated May 30, 2018, 10 pages.

* cited by examiner

INTEGRATED PROCESS FOR PRODUCTION OF GLYCEROL CARBONATE (4-HYDROXYMETHYL-2-OXO-1, 3-DIOXOLANE) AND UREA

CROSS REFERENCE TO RELATED APPLICATIONS

This application is a national phase application under 35 U.S.C. § 371 of International Application No. PCT/IB2018/051487 filed Mar. 7, 2018, which claims priority to U.S. Provisional Patent Application No. 62/484,276 filed Apr. 11, 2017. The entire contents of each of the above-referenced disclosures is specifically incorporated by reference herein without disclaimer.

FIELD OF INVENTION

The present invention generally relates to production of glycerol carbonate and/or urea. More specifically, the present invention relates to an integrated process of glycerol carbonate and/or urea production utilizing ammonia, carbon dioxide, and glycerol.

BACKGROUND OF THE INVENTION

In existing industrial processes, glycerol is formed as a byproduct of fatty acids and fatty alcohols production. Due to a recent increase in biofuels and biolubricants production, which generates an increased amount of glycerol, the current market for glycerol is over-saturated. Consequently, the price of glycerol has been driven down. In so far as many chemical companies see the risk of glycerol becoming chemical waste, a solution to integrate a process that consumes glycerol and generates products of higher value in traditional chemical facilities has become highly desirable.

Current chemical production processes that consume glycerol include manufacturing of glycerol carbonate (glycerine carbonate or 4-hydroxymethyl-2-oxo-1,3-dioxolane) from glycerol. For instance, U.S. Pat. No. 8,314,259 describes a glycerol carbonate production process using a lipase of bio-catalyst to react with a reactant solution, which is prepared by adding glycerol, a glycerol-containing composition, or a dimethyl carbonate in a reaction solvent. U.S. Pat. No. 6,025,504 discloses a method for producing glycerol carbonate from urea and glycerol using catalyst bearing Lewis acid sites. However, the capital expenditure and subsequent operating cost for these methods can be high, thereby limiting the economic feasibility of glycerol carbonate production.

BRIEF SUMMARY OF THE INVENTION

A method has been discovered for producing glycerol carbonate and/or urea. By integrating the process of glycerol carbonate production into a urea production process, ammonia generated during glycerol carbonate production may be re-used to produce urea, thereby reducing production cost.

Embodiments of the invention include a method of producing glycerol carbonate and/or urea. The method may comprise employing carbon dioxide and ammonia in synthesizing the urea. At least some of the urea may further react with glycerol to form glycerol carbamate and ammonia. The glycerol carbamate may be further decomposed to form the glycerol carbonate and ammonia. The method may further include feeding at least some of the ammonia from the reacting step and/or decomposing step to the step of employing carbon dioxide and ammonia in synthesizing the urea. The method may further include transferring any unreacted urea from the reacting step to a urea product stream and flowing the glycerol carbonate from the decomposing step in a glycerol carbonate product stream.

Embodiments of the invention include a method of producing glycerol carbonate and/or urea. The method may comprise employing carbon dioxide and ammonia in synthesizing the urea. The synthesizing may comprise the steps of reacting the ammonia with carbon dioxide to form ammonium carbamate, and decomposing the ammonium carbamate to form water and the urea. The method may further include reacting at least some of the urea with glycerol to form glycerol carbamate and ammonia. The method may further include decomposing the glycerol carbamate to form the glycerol carbonate and ammonia. The method may further include feeding at least some of the ammonia from the step of reacting urea with glycerol and/or the step of decomposing the glycerol carbamate to the urea synthesizing step. The method may further include transferring any unreacted urea from the step of reacting the urea with glycerol to a urea product stream, and flowing the glycerol carbonate from the step of decomposing the glycerol carbamate in a glycerol carbonate product stream.

Embodiments of the invention include a method of producing glycerol carbonate and/or urea. The method may comprise employing carbon dioxide and ammonia in synthesizing the urea. The synthesizing may comprise reacting the ammonia with the carbon dioxide to form ammonium carbamate, and decomposing the ammonium carbamate to form water and urea. The method may further include reacting at least some of the urea with glycerol to form glycerol carbamate and ammonia. The reacting comprises contacting the urea with the glycerol over a catalyst under reaction conditions sufficient to form the glycerol carbamate. The method may further include decomposing the glycerol carbamate to form the glycerol carbonate and ammonia. The method may further include feeding at least some of the ammonia from the step of reacting urea with glycerol and/or the step of decomposing the glycerol carbamate to the step of synthesizing the urea. The method may further include collecting any unreacted urea from the step of reacting urea with glycerol and concentrating the collected urea. The method may further include granulating concentrated urea from the step of concentrating the collected urea, and flowing the glycerol carbonate from the step of decomposing the glycerol carbamate in a glycerol carbonate product stream.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, twenty embodiments are now described. Embodiment 1 is a method of producing glycerol carbonate and/or urea, the method including steps as follows (1) employing carbon dioxide and ammonia in synthesizing the urea; (2) reacting at least some of the urea with glycerol to form glycerol carbamate and ammonia; (3) decomposing the glycerol carbamate to form the glycerol carbonate and ammonia; (4) feeding at least some of the ammonia from step (2) and/or step (3) to step (1) for the synthesizing; (5) transferring any unreacted urea from step (2) to a urea product stream; and (6) flowing the glycerol carbonate from step (3) in a glycerol carbonate product stream. Embodiment 2 is the method of embodiment 1, wherein step (1) comprises (a) reacting the ammonia with the carbon dioxide to form ammonium carbamate, and (b) decomposing the ammonium carbamate to form water and the urea. Embodiment 3 is the method of embodiment 2, wherein step (1) further comprises (c) heating the urea, unreacted ammonia and ammonium carbamate from steps (a) and (b) to further decompose ammonium carbamate and form urea and water; (d) concentrating the urea from the water and urea from steps (b) and (c); and (e) granulating the concentrated urea from step (d) to form granulated urea. Embodiment 4 is the method of any of the preceding embodiments, wherein the urea and glycerol in step (2) is provided at a molar ratio of 0.33:1 to 1.2:1. Embodiment 5 is the method of any of the preceding embodiments, wherein the steps (2) and (3) comprise contacting the urea with the glycerol over a catalyst under reaction conditions sufficient to form the glycerol carbonate. Embodiment 6 is the method of embodiment 5, wherein the reaction conditions comprise a reaction temperature in a range of 90° C. to 220° C. Embodiment 7 is the method of any of embodiments 5 and 6, wherein the reaction conditions comprise a reaction pressure in a range of $2.0 \times 10^{-5}$ to $2.0 \times 10^{-1}$ MPa. Embodiment 8 is the method of any of embodiments 5 to 7, wherein the reaction conditions comprise a batch time of 1 to 48 hours. Embodiment 9 is the method of any of embodiments 5 to 8, wherein the catalyst comprises a metal as a catalytically active species. Embodiment 10 is the method of embodiment 9, wherein the metal is selected from the group consisting of Zn++, Mg++, Mn++, Fe++, Ni++, Cd++, Ca++, Li+, and combinations thereof. Embodiment 11 is the method of any of embodiments 9 and 10, wherein the catalytically active species is present in one or more of sulfate, phosphate, stearates, carboxylates, derivative of natural fatty acids form, or combinations thereof. Embodiment 12 is the method of any of embodiments 9 to 11, where in the catalyst is calcined before step (2). Embodiment 13 is the method of any of embodiments 5 to 8, wherein the catalyst comprises a metal oxide as a catalytically active species. Embodiment 14 is the method of embodiment 13, wherein the metal oxide is selected from the group consisting of ZnO, $Co_3O_4$, CaO, $La_2O_3$, MgO, $ZrO_2$, and combinations thereof. Embodiment 15 is the method of any of embodiments 13 and 14, wherein the metal oxide is supported by a matrix, the matrix is selected from the group consisting of silica, alumina, hydrotalcite, polymers thereof, and combinations thereof. Embodiment 16 is the method of any of embodiments 5 to 8, wherein the catalyst includes a metal alkoxide based catalytic system comprising one or more titanium alkoxides, one or more aluminum alkoxides, one or more zirconium alkoxides, or combinations thereof. Embodiment 17 is the method of any of embodiments 5 to 8, wherein the catalyst includes an alkyl tin based catalytic system comprising dibutyltin oxide, dibutyltin dimethoxide, triphenyltin chloride, or combinations thereof. Embodiment 18 is the method of any of the preceding embodiments, wherein the urea and glycerol in step (2) reacts in a solvent. Embodiment 19 is the method of embodiment 18, wherein the solvent is selected from the group consisting of dimethylformamide, dimethyl sulfoxide, dichloromethane, nitrobenzene, dimethylacetamide, methanol, and combinations thereof. Embodiment 20 is the method of any of the preceding embodiments, further comprising steps as follows: (7) collecting any unreacted urea from step (2); (8) concentrating collected urea from step (7); and (9) granulating concentrated urea from step (8).

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for production of glycerol carbonate and/or urea. By integrating the process of glycerol carbonate production into a urea production process, ammonia generated during glycerol carbonate production is reused to produce urea, thereby reducing production cost for urea and providing a use for glycerol, thus, increasing its product value.

Glycerol carbonate has garnered a lot of commercial interest mainly due to its reactivity and wide range of applications. Because it can be produced from glycerol, glycerol carbonate can be a valuable product that helps absorb the current glycerol glut, and potentially increase profit margin of existing chemical plants that produce glycerol. However, none of the currently available methods of glycerol carbonate production are integrated into a chemical production process (e.g., urea production process) and fully take advantage of cheap feedstock readily available from common chemical plants. The discovered method, according to embodiments of the invention, may remedy these deficiencies.

Figure 1:
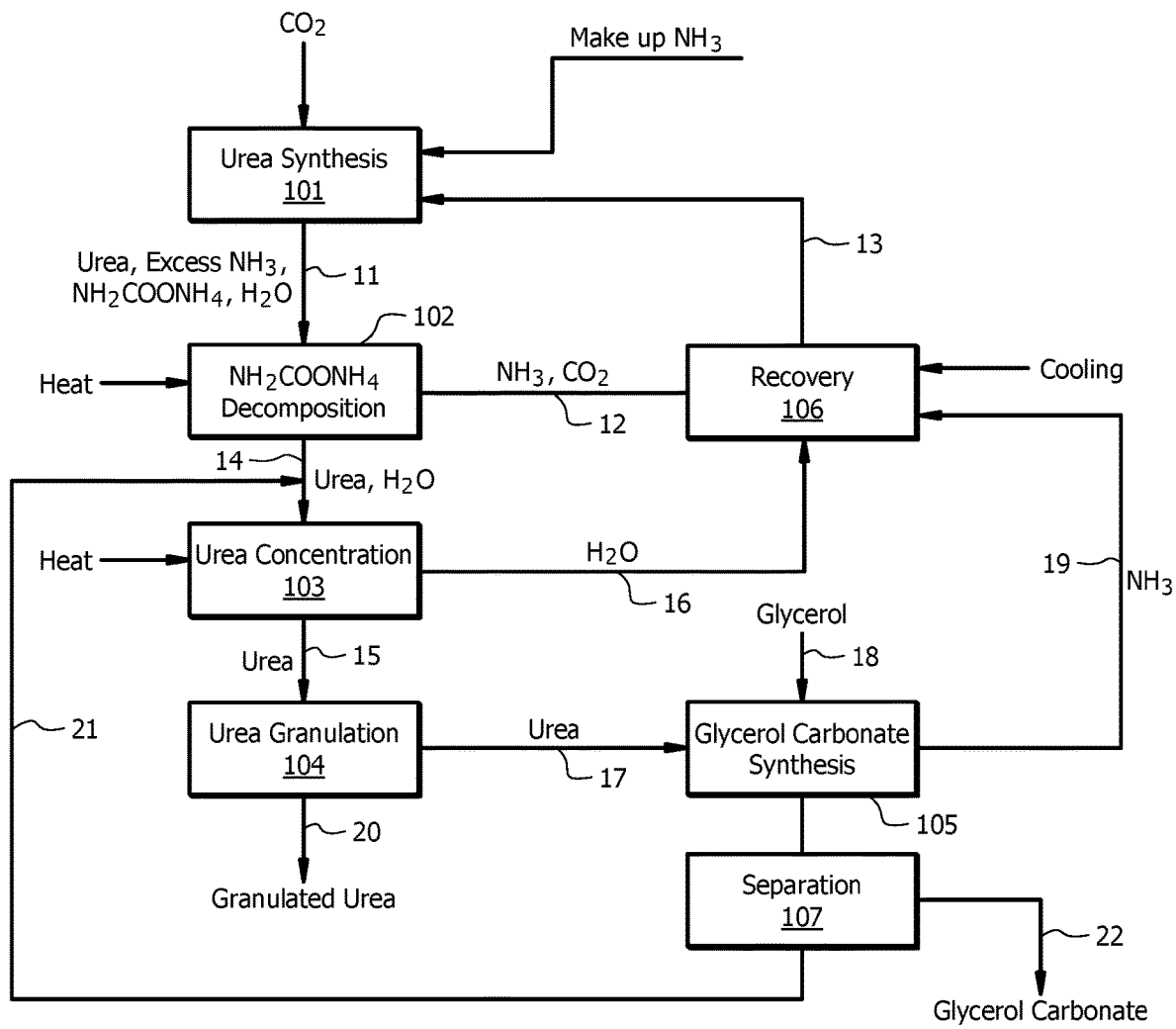
FIG. 1 is a flowchart for a method of producing glycerol carbonate and/or urea, according to embodiments of the invention.

As shown in FIG. 1, the embodiments of the present invention may employ carbon dioxide and ammonia in synthesizing urea via urea synthesis process 101. The synthesizing may comprise two main reactions:

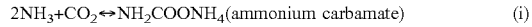

$$2NH_3 + CO_2 \leftrightarrow NH_2COONH_4 \text{(ammonium carbamate)} \quad \text{(i)}$$

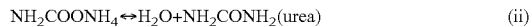

$$NH_2COONH_4 \leftrightarrow H_2O + NH_2CONH_2 \text{(urea)} \quad \text{(ii)}$$

In embodiments of the invention, the synthesizing of the urea may comprise reacting the ammonia with the carbon dioxide to form ammonium carbamate and decomposing the ammonium carbamate to form water and the urea. Thus, ammonium carbamate may be formed as a byproduct in urea synthesis process 101. First product stream 11 from urea synthesis process 101 may comprise urea, excess ammonia, ammonium carbamate, and water. In embodiments of the invention, first product stream 11 may comprise about 18 to 20 wt. % ammonia, about 50 to 52 wt. % ammonium carbamate, and about 30 to 35 wt. % urea.

First product stream 11 may be fed to ammonium carbamate decomposition process 102. In ammonium carbamate decomposition process 102, the ammonium carbamate in first product stream 11 may be decomposed into ammonia and carbon dioxide. In embodiments of the invention, ammonium carbamate decomposition process 102 may comprise heating the ammonia, ammonium carbamate and urea from first product stream 11 to a sequence of step wise decomposition temperatures of 200° C., 160° C., and 138° C., respectively. The ammonia and carbon dioxide generated from ammonium carbamate decomposition process 102 may form stream 12. Stream 12 may be fed back to urea synthesis process 101 in stream 13. The urea and water exiting the decomposition forms second product stream 14.

In embodiments of the invention, second product stream 14 comprising urea and water goes through urea concentration process 103 to produce molten urea of about 99.6 or 99.7 wt. % to 99.8 wt. %. The molten urea exiting urea concentration process 103 may form third product stream 15. In embodiments of the invention, urea concentration process 103 may comprise evaporating urea of 71 to 83.5 wt. % from stream 14 at 0.34 atmosphere absolute pressure. The evaporating process may comprise heating the urea and the water from second product stream 14 to a temperature of 110° C. to 130° C. In embodiments of the invention, the water generated in urea concentration process 103 may form stream 16. Stream 16 may be recycled back to urea synthesis process 101 in stream 13. Urea granulation process 104 may be performed on the urea from third product stream 15 to produce granulated urea 20.

With continued reference to FIG. 1, at least some of the urea produced from urea granulation process 104 may be loaded into a reactor system via stream 17. The reactor system contains glycerol that is loaded via stream 18. The urea and glycerol reacts under sufficient reaction conditions to produce glycerol carbonate via glycerol carbonate synthesis process 105. Generally, glycerol carbonate synthesis process 105 may comprise two main reactions:

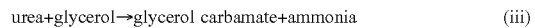

$$\text{urea} + \text{glycerol} \rightarrow \text{glycerol carbamate} + \text{ammonia} \quad \text{(iii)}$$

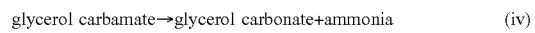

$$\text{glycerol carbamate} \rightarrow \text{glycerol carbonate} + \text{ammonia} \quad \text{(iv)}$$

In reaction (iii), the urea reacts with glycerol to form glycerol carbamate and ammonia. The glycerol carbamate is then decomposed to form glycerol carbonate and ammonia in reaction (iv).

In embodiments of the invention, the reaction conditions for glycerol carbonate synthesis process 105 may include a reaction temperature of about 90° C. to about 220° C., and all ranges and values there between including 90 to 100° C., or 100 to 110° C., or 110 to 120° C., or 120 to 130° C., or 130 to 140° C., or 140 to 150° C., or 150 to 160° C., or 160 to 170° C., or 170 to 180° C., or 180 to 190° C., or 190 to 200° C., or 200 to 210° C., or 210 to 220° C. The reaction conditions for glycerol carbonate synthesis process 105 may comprise a reaction pressure of about $2.0 \times 10^{-5}$ to $2.0 \times 10^{-1}$ MPa, and all ranges and values there between including $2.0 \times 10^{-5}$ to $2.0 \times 10^{-4}$ MPa, $2.0 \times 10^{-4}$ to $2.0 \times 10^{-3}$ MPa, $2.0 \times 10^{-3}$ to $2.0 \times 10^{-2}$ MPa, $2.0 \times 10^{-2}$ to $2.0 \times 10^{-1}$ MPa. In embodiments of the invention, the reaction conditions for glycerol carbonate synthesis process 105 may include a batch time (or residence time in the cases of non-batch reactors) of about 1 to about 48 hours depending on the catalyst used for the reaction and all ranges and values there between including 1 to 3 hours, 3 to 5 hours, 5 to 7 hours, 7 to 9 hours, 9 to 11 hours, 11 to 13 hours, 13 to 15 hours, 15 to 17 hours, 17 to 19 hours, 19 to 21 hours, 21 to 23 hours, 23 to 25 hours, 25 to 27 hours, 27 to 29 hours, 29 to 31 hours, 31 to 33 hours, 33 to 35 hours, 35 to 37 hours, 37 to 39 hours, 39 to 41 hours, 41 to 43 hours, 43 to 45 hours, or 45 to 48 hours.

In embodiments of the invention, a catalyst may be used in glycerol carbonate synthesis process 105. More specifically, the catalyst may comprise a metal as a catalytically active species. Exemplary metals may include, but are not limited to, one of Zn++, Mg++, Mn++, Fe++, Ni++, Cd++, Ca++, Li+, or combinations thereof. In embodiments of the invention, the metal may be present in sulfate, phosphate, stearates, carboxylates, derivative of natural fatty acids form or combinations thereof. The catalyst may be used in this reaction after calcination. Additionally or alternatively, the catalyst used in this reaction may comprise a metal oxide as a catalytically active species. Examples of the metal oxide may include, but are not limited to, one of ZnO, Co$_3$O$_4$, CaO, La$_2$O$_3$, MgO, ZrO$_2$, or combinations thereof. Additionally or alternatively, the catalyst used in this reaction may comprise a metal alkoxide based catalytic system. The metal alkoxide based catalytic system may include one or more titanium alkoxides, one or more aluminum alkoxides, one or more zirconium alkoxides, or combinations thereof. Additionally or alternatively, the catalyst used in this reaction may comprise a alkyl tin based catalytic system. The alkyl tin based catalytic system may include dibutyltin oxide, dibutyltin dimethoxide, triphenyltin chloride, or combinations thereof. In embodiments of the invention, the metal oxide (catalytically active species) may be supported by a matrix. This matrix may be one of silica, alumina, hydrotalcite, polymers thereof, or combinations thereof. In embodiments of the invention, a solvent may be used in glycerol carbonate synthesis process 105. Exemplary solvents may include, but are not limited to, one of dimethylformamide, dimethyl sulfoxide, dichloromethane, nitro-benzene, dimethylacetamide, methanol, or combinations thereof.

In embodiments of the invention, the molar ratio of urea to glycerol provided in process 105 may include about 0.33 to about 1.2, and all ranges and values there between, including 0.33 to 0.40, 0.40 to 0.50, 0.50 to 0.60, 0.60 to 0.70, 0.70 to 0.80, 0.80 to 0.90, 0.90 to 1.00, 1.00 to 1.10, or 1.10 to 1.20. In embodiments of the invention, the molar ratio of urea to glycerol in process 105 may include 0.33 to 0.40, or 0.40 to 0.50, 0.50 to 0.60, 0.60 to 0.70, 0.70 to 0.80, 0.80 to 0.90, 0.90 to 1.00, 1.00 to 1.10, or 1.10 to 1.20, and all ranges and values there between.

In embodiments of the invention, the ammonia produced from glycerol carbonate synthesis process 105 may be recycled back to the urea synthesis reaction via stream 19. In embodiments of the invention, ammonia from streams 12 and 19, carbon dioxide from stream 12, and water from stream 16 may be recovered via recovery process 106, and subsequently fed back to urea synthesis process 101 via stream 13. The recovery process 106 may comprise cooling the ammonia from streams 12 and 19, the carbon dioxide from stream 12 and the water from stream 16 via cooling tower, chiller, or a combination thereof.

In embodiments of the present invention, unreacted urea from glycerol carbonate synthesis process 105 may be separated from the glycerol carbonate via separation process 107. The separated, unreacted urea may be collected and returned to second product stream 14 via stream 21. Alternatively or additionally, the separated, unreacted urea may be collected and directly returned to urea concentration process 103. The unreacted urea may be further concentrated via urea concentration process 103, and granulated via urea granulation process 104. In embodiments of the invention, separation process 107 may include one or more of filtration, vacuum distillation, carbon bed adsorption, or combinations thereof. Alternatively, the urea from glycerol carbonate synthesis process 105 may be substantially fully reacted and may not be recycled back to second product stream 14. In embodiments of the invention, the glycerol carbonate may be collected via fifth product stream 22 after separation process 107.

Figure 2:
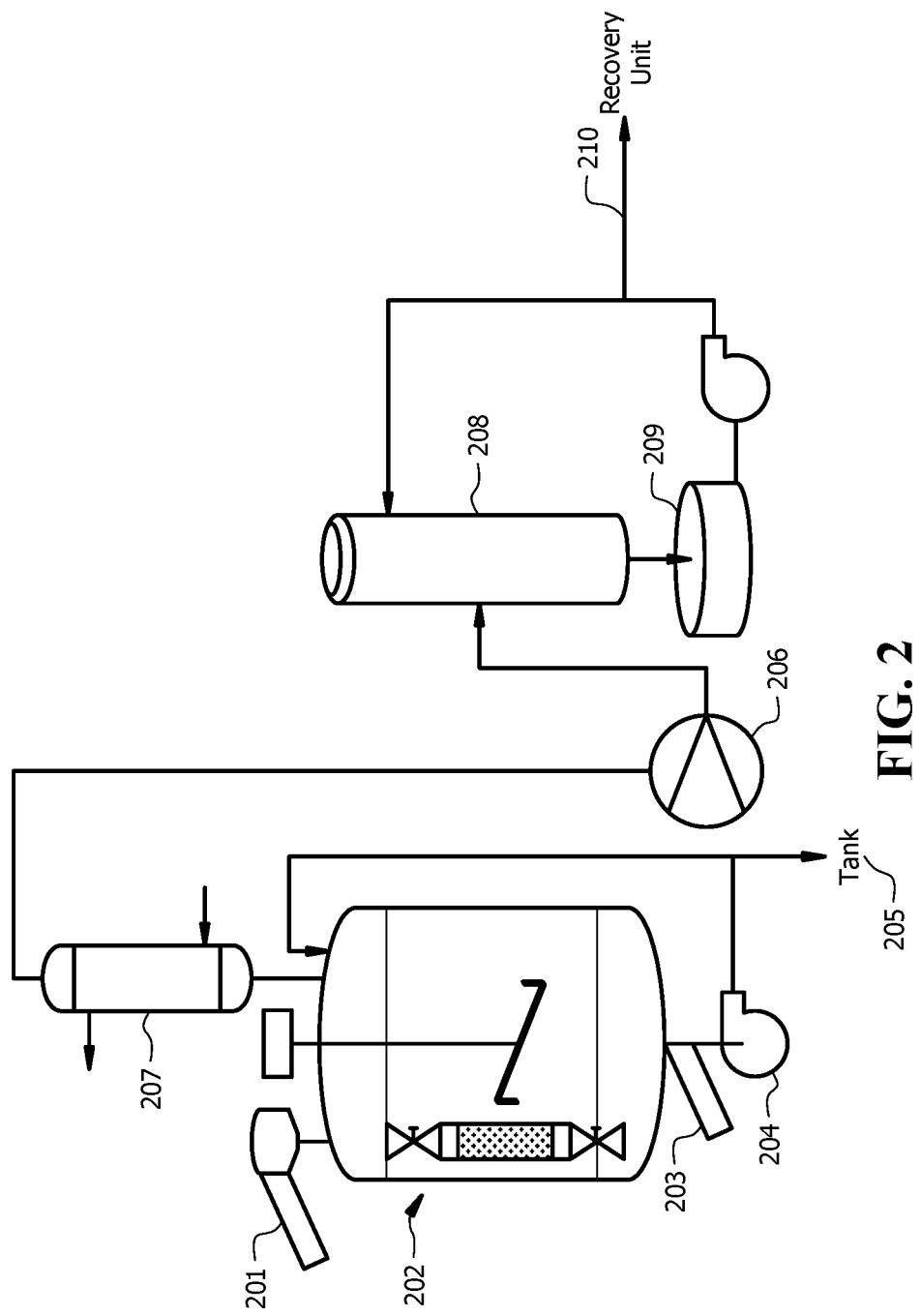
FIG. 2 is a schematic diagram for a reactor system used for producing glycerol carbonate and/or urea, according to embodiments of the invention.

As shown in FIG. 2, the reactor system for production of glycerol carbonate may comprise solid loading conveyor 201 connected to reaction vessel 202. Granulated urea can be loaded into reaction vessel 202 through solid loading conveyor 201. Once the granulated urea comes into contact with the glycerol in reaction vessel 202, agitation and thermal treatment may be applied to the mixture. Solvents and/or catalyst described above may be applied in reaction vessel 202 for glycerol carbonate synthesis 105.

The product stream comprising glycerol carbonate, unreacted urea, and/or glycerol carbamate exiting the reaction vessel may go through solids removal filtration facility 203. The liquid glycerol carbonate may be either recycled back to the reaction vessel through liquid recycle pump 204 or collected as the product having 90 to 94 wt. % glycerol carbonate in storage tank 205. The ammonia generated in glycerol carbonate process 105 may be removed using vacuum pump 206. To avoid the glycerol carbonate entering the vacuum line, condenser 207 may be installed before vacuum pump 206. Glycerol carbonate vapor drawn by vacuum pump 206 may be condensed and returned to reaction vessel 202. The ammonia removed from reaction vessel 202 by vacuum pump 206 may be scrubbed in water scrubber 208, where it is absorbed and then transferred to ammonia solution tank 209. The ammonia solution is then transferred to ammonia recovery unit 210. The recovered ammonia may be recycled back to urea synthesis process 101.

Although embodiments of the present invention have been described with reference to blocks of FIG. 1, it should be appreciated that operation of the present invention is not limited to the particular blocks and/or the particular order of the blocks illustrated in FIG. 1. Accordingly, embodiments of the invention may provide functionality as described herein using various blocks in a sequence different than that of FIG. 1.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing glycerol carbonate and/or urea, the method comprising steps as follows:
    (1) reacting carbon dioxide and ammonia to produce a first product stream comprising ammonium carbamate, unreacted ammonia, water and the urea;
    (2) heating the first product stream to decompose the ammonium carbamate to form a first decomposition product stream comprising ammonia and carbon dioxide, and a second product stream comprising urea and water;
    (3) subjecting the second product stream to a concentration process to produce a third product stream comprising concentrated urea;
    (4) subjecting the third product stream comprising the concentrated urea to a granulation process to produce granulated urea;
    (5) reacting at least some of the granulated urea with glycerol to form glycerol carbamate and ammonia;
    (6) decomposing the glycerol carbamate to form the glycerol carbonate and ammonia;
    (7) feeding at least some of the ammonia from step (5) and/or step (6) to step (1) for the reacting to form the first product stream;
    (8) transferring any unreacted granulated urea from step (5) to a urea product stream; and
    (9) flowing the glycerol carbonate from step (6) in a glycerol carbonate product stream;
    wherein the steps (5) and (6) comprise contacting the urea with the glycerol over a catalyst under reaction conditions sufficient to form the glycerol carbonate; and
    wherein the reaction conditions in step (5) comprise a reaction temperature in a range of 90° C. to 220° C. and a reaction pressure in a range of $2.0 \times 10^{-3}$ to $2.0 \times 10^{-1}$ MPa; and wherein the method is an integrated method for the production of glycerol carbonate and/or urea;

wherein the catalyst comprises a metal as a catalytically active species; and wherein the metal is a single member selected from the group consisting of $Zn^{++}$, $Mg^{++}$, $Mn^{++}$, $Fe^{++}$, $Ni^{++}$, $Cd^{++}$, $Ca^{++}$ and $Li^+$, or is a combination of any two or more of $Zn^{++}$, $Mg^{++}$, $Mn^{++}$, $Fe^{++}$, $Ni^{++}$, $Cd^{++}$, $Ca^{++}$ and $Li^+$.

2. The method of claim 1, wherein the metal is $Mg^{++}$.
3. The method of claim 1, wherein the metal is $Mn^{++}$.
4. The method of claim 1, wherein the metal is $Fe^{++}$.
5. The method of claim 1, wherein the metal is $Ni^{++}$.
6. The method of claim 1, wherein the metal is $Li^+$.
7. A method of producing glycerol carbonate and/or urea, the method comprising steps as follows:
   (1) employing carbon dioxide and ammonia in synthesizing the urea;
   (2) reacting at least some of the urea with glycerol to form glycerol carbamate and ammonia;
   (3) decomposing the glycerol carbamate to form the glycerol carbonate and ammonia;
   (4) feeding at least some of the ammonia from step (2) and/or step (3) to step (1) for the synthesizing;
   (5) transferring any unreacted urea from step (2) to a urea product stream; and
   (6) flowing the glycerol carbonate from step (3) in a glycerol carbonate product stream;
   wherein the urea and glycerol in step (2) reacts in a solvent;
   wherein the steps (2) and (3) comprise contacting the urea with the glycerol over a catalyst under reaction conditions sufficient to form the glycerol carbonate; and
   wherein the reaction conditions comprise a reaction temperature in a range of 90° C. to 220° C. and a reaction pressure in a range of $2.0 \times 10^{-3}$ to $2.0 \times 10^{-1}$ MPa;
   wherein the method is an integrated method for glycerol carbonate and/or urea; and
   wherein the solvent is selected from the group consisting of dichloromethane, nitro-benzene, methanol, and combinations thereof.

8. The method of claim 2, wherein the metal consists of $Zn^{++}$.

9. The method of claim 1, wherein the reaction conditions comprise a reaction temperature in a range of 190° C. to 220° C.

10. The method of claim 7, wherein the solvent is dichloromethane, methanol, or a combination thereof.

11. A method for producing glycerol carbonate, the method comprising steps of:
   loading granulated urea into a reaction vessel via a solid loading conveyor connected to the reaction vessel, wherein the reaction vessel contains glycerol, to form a reaction mixture;
   agitating and thermally treating the reaction mixture in the reaction vessel to produce a product stream comprising the glycerol carbonate, unreacted urea and glycerol carbamate;
   feeding the product stream to a solids removal filtration facility; and
   collecting the glycerol carbonate in a storage tank or recycling the glycerol carbonate to the reaction vessel.

12. The method of claim 11, wherein a solvent, a catalyst or both are added to the reaction vessel.

13. The method of claim 11, wherein product stream is fed through a solids removal filtration facility.

14. The method of claim 11, wherein ammonia produced in the reaction vessel is removed from the reaction vessel via a vacuum pump.

15. The method of claim 14, wherein a condenser is installed before the vacuum pump to condense glycerol carbonate vapor drawn by the vacuum pump.

16. The method of claim 14, wherein the ammonia is scrubbed in a water scrubber.

* * * * *